(12) United States Patent
Zhong

(10) Patent No.: US 6,468,649 B1
(45) Date of Patent: Oct. 22, 2002

(54) ANTIMICROBIAL ADHESION SURFACE

(75) Inventor: Samuel P. Zhong, Northboro, MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/457,955

(22) Filed: Dec. 9, 1999

Related U.S. Application Data

(60) Continuation-in-part of application No. 08/929,948, filed on Sep. 15, 1997, now Pat. No. 6,045,620, which is a division of application No. 08/392,141, filed on Feb. 22, 1995, now Pat. No. 5,702,754.

(51) Int. Cl.$^7$ ................................................ B32B 5/16
(52) U.S. Cl. .................... 428/341; 428/340; 428/413; 428/420
(58) Field of Search ...................... 428/36.9, 36.91, 428/36.92, 341, 413, 340, 420; 524/589, 590, 874; 623/11, 12

(56) References Cited

U.S. PATENT DOCUMENTS

| | | |
|---|---|---|
| 3,663,288 A | 5/1972 | Miller |
| 3,779,792 A | 12/1973 | Stoy et al. |
| 4,047,957 A | 9/1977 | DeWinter et al. |
| 4,100,309 A | 7/1978 | Micklus et al. |
| 4,119,094 A | 10/1978 | Micklus et al. |
| 4,263,188 A | 4/1981 | Hampton et al. |
| 4,306,998 A | 12/1981 | Wenzel et al. |
| 4,373,009 A | 2/1983 | Winn |
| 4,387,024 A | 6/1983 | Kurihara et al. |
| 4,459,317 A | 7/1984 | Lambert |
| 4,536,179 A | 8/1985 | Anderson et al. |
| 4,548,844 A | 10/1985 | Podel et al. |
| 4,642,267 A | 2/1987 | Creasy et al. |
| 4,666,437 A | 5/1987 | Lambert |
| 4,675,361 A | 6/1987 | Ward, Jr. |
| 4,692,352 A | 9/1987 | Huddleston |
| 4,705,709 A | 11/1987 | Vailancourt |
| 4,721,117 A | 1/1988 | Mar et al. |
| 4,748,986 A | 6/1988 | Morrison et al. |
| 4,833,014 A | 5/1989 | Linder et al. |
| 4,841,976 A | 6/1989 | Packard et al. |
| 4,867,173 A | 9/1989 | Leoni |
| 4,876,126 A | 10/1989 | Takemura et al. |
| 4,884,579 A | 12/1989 | Engelson |
| 4,925,698 A | 5/1990 | Klausner et al. |
| 4,943,460 A | 7/1990 | Markle et al. |
| 4,959,074 A | 9/1990 | Halpern et al. |
| 4,964,409 A | 10/1990 | Tremulis |
| 4,980,231 A | 12/1990 | Baker et al. |
| 5,002,582 A | 3/1991 | Guire et al. |
| 5,007,928 A | 4/1991 | Okamura et al. |
| 5,008,363 A | 4/1991 | Mallon et al. |
| 5,026,607 A | 6/1991 | Kiezulas |
| 5,037,656 A | 8/1991 | Pitt et al. |
| 5,037,677 A | 8/1991 | Halpern et al. |
| 5,040,543 A | 8/1991 | Badera et al. |
| 5,049,403 A | 9/1991 | Larm et al. |
| 5,057,371 A | 10/1991 | Canty et al. |
| 5,066,705 A | 11/1991 | Wickert |
| 5,067,489 A | 11/1991 | Lind |
| 5,069,217 A | 12/1991 | Fleishhacker, Jr. |
| 5,069,226 A | 12/1991 | Yamauchi et al. |
| 5,079,093 A | 1/1992 | Akashi et al. |
| 5,080,683 A | 1/1992 | Šulc et al. |
| 5,080,924 A | 1/1992 | Kamel et al. |
| 5,084,315 A | 1/1992 | Karimi et al. |
| 5,091,205 A | 2/1992 | Fan |
| 5,102,401 A | 4/1992 | Lambert et al. |
| 5,105,010 A | 4/1992 | Sundararaman et al. |
| 5,107,852 A | 4/1992 | Davidson et al. |
| 5,128,170 A | 7/1992 | Matsuda et al. |
| 5,129,890 A | 7/1992 | Bates et al. |
| 5,160,790 A | 11/1992 | Elton |
| 5,211,183 A | 5/1993 | Wilson |
| 5,213,111 A | 5/1993 | Cook et al. |

(List continued on next page.)

FOREIGN PATENT DOCUMENTS

| | | |
|---|---|---|
| AU | 1 435 797 U.K | 5/1976 |
| AU | 556350 | 9/1986 |
| AU | 556351 | 9/1986 |
| EP | 0 093 094 | 11/1983 |
| EP | 0 106 004 | 4/1984 |
| EP | 0 166 998 | 1/1986 |
| EP | 0 389 632 | 10/1990 |
| EP | 0 395 098 | 10/1990 |
| EP | 0 407 965 A1 | 1/1991 |
| EP | 0 439 908 A1 | 8/1991 |
| EP | 0 480 809 A2 | 4/1992 |
| EP | 0 592 870 A1 | 9/1993 |
| EP | 0 611 576 A1 | 2/1994 |
| UA | 2 128 500 A | 5/1984 |
| WO | pct/dk91/00163 | 12/1991 |
| WO | pct/us92/09073 | 10/1992 |

OTHER PUBLICATIONS

PEBAX ® 3533 SA 00 Base polymer for Structural Hot Melt Adhesives.

STS Biopolymers Literature, Medical Device Coatings, pp 1–3, dated Sep. 15, 1999.

C.R. Bard Inc. Literature, Bard Medicall Division, pp 1–2, dated Sep. 14, 1999.

Sur Modics Inc. Literature, Wt Lubriciy & Antimicrobial Properties, pp 1–2, dated Sep. 15, 1999.

Gabriel et al., Uncover Urinary Tract Infections, 1997.

Primary Examiner—Merrick Dixon
(74) Attorney, Agent, or Firm—Kenyon & Kenyon

(57) ABSTRACT

The present invention provides an implantable medical device having a substrate with a hydrophilic coating composition to limit in vivo colonization of bacteria and fungi. The hydrophilic coating composition includes a hydrophilic polymer with a molecular weight in the range from about 100,000 to about 15 million selected from copolymers acrylic acid, methacrylic acid, isocrotonic acid and combinations thereof.

32 Claims, No Drawings

U.S. PATENT DOCUMENTS

| | | |
|---|---|---|
| 5,217,026 A | 6/1993 | Stoy et al. |
| 5,240,994 A | 8/1993 | Brink et al. |
| 5,241,970 A | 9/1993 | Johlin, Jr. et al. |
| 5,243,996 A | 9/1993 | Hall |
| 5,250,613 A | 10/1993 | Bergstrom et al. |
| 5,266,359 A | 11/1993 | Spielvogel |
| 5,275,173 A | 1/1994 | Samson et al. |
| 5,290,585 A | 3/1994 | Elton |
| 5,304,140 A | 4/1994 | Kugo et al. |
| 5,322,520 A | 6/1994 | Milder |
| 5,328,954 A * | 7/1994 | Sarangapani ............... 524/589 |
| 5,366,505 A * | 11/1994 | Farber ......................... 623/11 |
| 5,567,495 A * | 10/1996 | Modak et al. ............. 428/36.9 |
| 5,576,072 A | 11/1996 | Hostettler et al. |
| 5,716,406 A * | 2/1998 | Farber ......................... 623/11 |
| 5,776,611 A * | 7/1998 | Elton ...................... 428/423.1 |
| 5,902,283 A * | 5/1999 | Darouiche et al. .......... 604/265 |

* cited by examiner

ANTIMICROBIAL ADHESION SURFACE

CROSS-REFERENCE TO RELATED APPLICATIONS

This application is a continuation-in-part of U.S. Ser. No. 08/929,948, U.S. Pat. No. 6,045,620 filed Sep. 15, 1997, which is a Divisional of U.S. Ser. No. 08/392,141, filed Feb. 22, 1995, now U.S. Pat. No. 5,702,754, which are both incorporated by reference herein.

FIELD OF THE INVENTION

This invention relates to a composition and a method for inhibiting adherence and growth of microorganisms on surfaces of implantable medical devices. More particularly, the present invention provides a substrate with a hydrophilic coating that becomes lubricous when contacted with an aqueous fluid to inhibit adherence and multiplication of microorganisms on the coating.

BACKGROUND OF THE RELATED TECHNOLOGY

There are a number of medical devices that are used in an environment where microorganisms, for instance bacteria, may be present on the surface of the device to cause device-related infection or biofilm formation. A few common, but nonlimiting, examples of such devices include ureteral stents, central venous catheters and ureteral catheters.

Bacterial colonization of indwelling and implantable medical devices may often lead to serious and sometimes fatal infections. For instance, urethral catheterization contributes to a high incidence of nosocomial urinary tract infections. Many patients who have an indwelling catheter for more than five days often develop a bacterial colonization of the bladder. Such colonization can lead to bacteremia, including septicemia, in hospitalized patients. Furthermore, the colonization of bacteria on the surfaces of a catheter may also result in the need to remove and/or replace the implanted device and to subsequently treat secondary infective conditions.

One technique to reduce microbial colonization on indwelling medical devices, such as catheters, is to impregnate the medical device with one or more antimicrobial agents to inhibit the growth of bacterial and fungal organisms, such as staphylococci, other gram-positive bacteria, gram-negative bacilli and Candida. Various methods have previously been employed to coat or impregnate antibiotics onto the surfaces of medical devices. Classes of antibiotics used include tetracyclines, rifamycins, macrolides, penicillins, cephalosporins, other beta-lactam antibiotics (i.e. imipenem, aztreonam), aminoglycosides, chloramphenicol, sufonamides, glycopeptides, quinolones, fusidic acid, trimethoprim, metronidazole, clindamycin, mupirocin, polyenes, azoles and beta-lactam inhibitors (i.e. sulbactam). For example, one method to coat a medical device is to simply flush the surface of the device with a solution of antibiotics.

Medical devices have also been coated with oligodynamic metals, such as silver, for use as antibacterial agents. For instance, catheters with silver impregnated in a soluble collagen or polymer coating are known. After these silver-coated catheters are placed at an in vivo location, the coating slowly dissolves to release silver ions which have a bactericidal effect against some types of bacteria. Furthermore, other iontophoretic medical devices use an electrical current derived from dissimilar galvanic materials to drive oligodynamic metal ions into solution to kill bacteria.

Furthermore, salicylic acid or its salts, and other nonsteroidal anti-inflammatory drugs ("NSAIDS") have been used to retard the adherence of bacteria onto surfaces of medical devices, thereby preventing colonization of bacteria. Such materials may be coated onto or be impregnated into the surface of a medical device.

The practices of coating or incorporating antibiotics, oligodynamic metals, salicylates, NSAIDS and the like onto the surface of medical devices do not often provide long term efficacy. While such coated or impregnated surfaces may provide somewhat effective protection initially against bacteria, the antibacterial effectiveness declines over time. During the in vivo use of the medical device, the antibacterial materials leach from the surface of the device into the surrounding environment. Over a period of time, the amount of antibacterial material present on the surface decreases to a point where the protection against bacteria is no longer effective. Furthermore, the in vivo release of antibiotics, oligodynamic metals, salicylates, NSAIDS and the like may result in adverse effects in some patients under certain conditions.

Accordingly, there is a need for a medical device that can remain in vivo for extended periods of time without losing its antimicrobial efficacy. There is also a need for a medical device, such as a catheter, an implant, or other indwelling device, which provides protection against bacterial and fungal organisms for extended periods of time without leaching substances into a patient.

SUMMARY OF THE INVENTION

The present invention provides medical devices, such as implantable devices, catheters, guidewires and the like, having a substrate or a portion of a substrate with a hydrophilic coating composition. The hydrophilic coating composition becomes disaffinitive to microbes upon contact with an aqueous fluid to limit in vivo colonization of microbes for extended periods of time to less than 10,000 cfu/mm$^2$ thereat.

In one aspect of the present invention, the hydrophilic coating composition includes a hydrophilic polymer selected from copolymers acrylic acid, methacrylic acid, isocrotonic acid and combinations thereof. The hydrophilic polymer has a molecular weight in the range from about 100,000 to about 15 million. One useful hydrophilic polymer is an acrylamide-acrylic acid copolymer.

In another aspect of the present invention, the hydrophilic coating compositions inhibits primary adherence to medical devices of spherical bacterial, rod-shaped bacterial, spiral bacteria, fungi and combinations thereof.

In another aspect of the present invention, a method to limit in vivo the primary adherence of microbes of implanted medical devices is provided. The method includes coating a medical device with the hydrophilic polymer of the present invention.

DETAILED DESCRIPTION OF THE INVENTION

The present invention is an implantable medical device with a hydrophilic coating composition or surface to limit or inhibit adhesion of microbes or microorganisms thereat. The hydrophilic surface becomes disaffinitive to microbes upon contact with an aqueous fluid to limit microbial adherence. By inhibiting or limiting microbial adhesion, the risk of infection associated with indwelling medical devices is reduced. The present invention also includes a method for limiting microbial adherence to the surfaces of medical devices.

As used herein the terms "microbe", "microorganism" and their variants are used interchangeably and refer to unicellular or small multicellular organisms, including bacteria, fungi, protozoa and viruses. As used herein, the terms "bacteria" and "fungi" refer to all genuses and species of bacteria and fungi, including but not limited to all spherical, rod-shaped and spiral bacteria. Some nonlimiting examples of bacteria are staphylococci (i.e. *Staphylococcus epidermidis, Staphylococcus aureus*), *Enterrococcus faecalis, Pseudomonas aeruginosa, Escherichia coli*, other gram-positive bacteria and gram-negative bacilli. One example of a fungus is *Candida albicans*.

Generally, microorganisms can exist in two distinct physical states. In a planktonic or floating state, microbial cells function as individuals. In an sessile or adherent state, the microbial cells attach to a surfaces (primary adherence) and multiply in quantity (colonization) on the surface of the medical device.

Many bacteria and fungi have surface polysaccharides. These surface polysaccharides generate a glycocalyx that surrounds the microbe and portions of the adhering surface. The glycocalyx consists of a mass of long polysaccharide fibers. This mass is often referred to as a extracellular slime or simply a slime. The production of surface polysaccharide or slime by an microorganism enables it to adhere to surfaces of insertable or implantable devices. The glycocalyx surrounds individual microorganisms or colonies of microorganisms offering protection against phagocytes and biocides while also providing a suitable environment for the transport of nutrients.

As the microorganisms multiple, a biofilm or a dense population of microorganisms is formed on a surface of a medical device. Groups of multiplied microorganisms are often referred to as colonies. As used herein, the term "colony" and it variants refer to a group of microorganisms formed from the multiplication of smaller number of microorganisms. Once formed, the biofilm continues to be a source for the spread of infection to other parts of the body by microbe detachment and biofilm sloughing.

The bacterial biofilms consist of micro-colonies surrounded by polysaccharide produced by the bacteria. The biofilms and portions of the cell walls of the bacteria are hydrophobic. This hydrophobic characteristic is apparently due to the presence of oligosaccharides within the biofilms and the cellular walls.

The medical devices that are amenable to the antimicrobial adhesion surface of the present invention generally include any medical device suitable for implantation or indwelling, as well as those used for minimally invasive procedures such as catheters, guidewires and the like. Non-limiting examples of medical devices include peripherally insertable central venous catheters, dialysis catheters, long term tunneled central venous catheters, peripheral venous catheters, short-term central venous catheters, arterial catheters, pulmonary artery catheters, urinary catheters, long term urinary devices, tissue bonding urinary devices, penile prostheses, vascular grafts, endovascular grafts, vascular catheter ports, wound drain tubes, hydrocephalus shunts, peritoneal catheters, artificial urinary sphincters, urinary dilators, guidewires, ureteral stents, vascular stents and the like.

The hydrophilic surface of the present invention contains a lubricous, hydrophilic polymer. The ability to become lubricous, i.e. become hydrated, is a critical aspect of the present invention. The degree of lubricity produced upon contact with aqueous medium will depend on a number of factors, including the type of hydrophilic polymer, its molecular weight, the exposure level to the aqueous medium, as well as the presence of agents which facilitate wetting. Among these, the molecular weight is the most important. The molecular weight range useful in the present invention will depend on the particular type of polymer chosen. The molecular weight of the hydrophilic polymer in the hydrophilic coating composition will typically be in the range from about 100,000 to about 15 million, particularly from about 150,000 to about 10 million. Hydrophilic polymers having a molecular weight in the range from about 400,000 to about 10 million and particularly of approximately 7.5 million have been found particularly useful in the present invention. Acrylamide-acrylic acid copolymer is a useful hydrophilic polymer which falls within this useful range of molecular weight.

The hydrophilic coating composition is sufficiently lubricous upon contact with an aqueous fluid to inhibit the in vivo adherence of microbes. The lubricous nature of the composition limits surface adhering microbes to inhibit the formation of slime and the formation of a biofilm. Furthermore, the hydrophilic nature of the coating composition is sufficiently repulsive to bacteria and their biofilms due to hydrophobic-hydrophilic interactions resulting from forces, such as ionic forces. The hydrophilic coating composition upon contact with an aqueous fluid is disaffinitive to bacteria and biofilms for extended periods of time. As used herein, the term "disaffinitive" and its variants refer to a repellent nature of one substance towards another substance to substantially prevent affixation of the substances therebetween. As a result of these characteristics, the risk of infection is reduced with use of medical devices having the hydrophilic coating composition of the present invention.

One means to characterize the lubricity of the inventive composition upon contact with aqueous medium is to determine a resistance to movement or a coefficient of friction. The coefficient of friction can be determined through well-known techniques and devices. For instance, a portion of a medical device is placed in a tube filled with saline to hydrate the device. The upper part on the device is connected to a Chattilon Tension tester. A set of rollers is placed directly above the tube in a manner such that hydrated portion of the medical device goes through the set of rollers. A weight is accurately applied to the roller surface through a sliding mechanism. A Chattilon force gauge and a driving motor are engaged. The hydrated medical device is then pulled through the set of rollers. As soon as the hydrated portion of the medical device coated with the hydrophilic polymer passes the set of rollers, the pulling force on the gauge is recorded. The coefficient of friction is determined from the pulling force and the weight applied to the surface. The coefficient of friction equals the pulling force divided by the weight applied to the surface. The hydration time for the coating is typically thirty seconds before commencing the Chattilon Tension Tester. The typical pulling speed through the set of rollers is 6 inches per minute.

A medical device coated with the hydrophilic polymer of the present invention was tested in a Chattilon tension tester as described above. The weight applied to the surface was 400 grams. The pulling force measured by the Chattilon gauge was 11.2 grams. The calculated coefficient of friction was 0.028. Under similar test conditions the same medical, but without being coated with the hydrophilic polymer of the present invention, was tested to have a calculated coefficient of friction of greater than 0.375.

In one aspect of the present invention, medical devices and particularly implantable devices, having a substrate or a portion of a substrate with a hydrophilic coating composition which becomes lubricous upon contact with an aqueous fluid is provided. The hydrophilic coating composition contains a hydrophilic polymer having a lubricity upon contact with an aqueous fluid from about 0.02 to about 0.2 coefficient of friction. The hydrophilic coating composition limits in vivo adherence of microbes on the coating from to less that 10,000 colony forming units ("cfu") per square millimeter ($mm^2$) at the surface of the coating for extended periods of time, for instance from about 5 to about 30 days or greater.

The hydrophilic coating composition of the present invention showed little or no bacterial adhesion as compared to other commercially available hydrogel coated surfaces or a non-hydrogel coated surface. Other commercially available hydrogel coated samples had greater than 10,000,000 cfu/$mm^2$ of *Escherichia coli* during a 5 through 30 day test period under a bacterial adhesion test. These levels of colony forming units resulted in bacterial coverage (or biofilm formation) of 80 percent or greater of the surface of the tested samples. The substrate coated with the hydrophilic coating composition of the present invention showed no bacterial adhesion under the same test conditions.

The hydrophillic coating composition of the present invention also proved effective against colonization of *Staphylococcus epidermidis* and *Pseudomonas aeruginosa* bacteria. The hydrophilic coating composition of the present invention showed no bacterial adhesion after a 5 day test period as compared to significant bacterial coverage of greater the 10,000,000 cfu/$mm^2$ for a substrate not having the hydrophilic coating composition of the present invention. This uncoated substrate had its entire surface covered with biofilms.

Desirably, the hydrophilic coating composition of the present invention substantially limits in vivo bacterial adhesion to a coated substrate at a quantity less than 10,000 cfu/$mm^2$ and less than 40 percent coverage of the surface of the coated substrate. More desirably, the hydrophilic coating composition of the present invention substantially limits in vivo bacterial adhesion to a coated substrate at a quantity less than 1,000 cfu/$mm^2$ and less than 20 percent coverage of the surface of the coated substrate. Even more desirably, the hydrophilic coating composition of the present invention substantially limits in vivo bacterial adhesion to a coated substrate at a quantity less than 100 cfu/$mm^2$ and less than 10 percent coverage of the surface of the coated substrate.

In another aspect of the present invention, a method for limiting colonization of microbes on a substrate of medical devices, and particularly implantable devices, is provided. The method comprises the steps of selecting a hydrophilic polymer having a disaffinity to microbes upon contact with an aqueous fluid; and coating the substrate with said hydrophilic polymer; wherein the hydrophilic polymer limits in vivo adherence of microbes on the coated substrate to less than 10,000 cfu/ mm2 and a biofilm coverage of less than 40 percent.

The hydrophilic surface on the medical device may be suitably formed by (a) coating a substrate with a first aqueous coating composition comprising an aqueous dispersion or emulsion of a polymer having organic acid functional groups and an excess of a polyfunctional crosslinking agent having functional groups which reacts with organic acid groups, and drying the coating to obtain a substantially water-insoluble coating layer still including functional groups being reactive with organic acid groups, and (b) contacting the dried coating layer obtained in (a) with a second aqueous coating composition comprising an aqueous solution or dispersion of a hydrophilic polymer having organic acid functional groups, and drying the combined coating, the hydrophilic polymer thereby becoming covalently bonded to the polymer of the first coating composition through the excess crosslinking agent. As used herein, the phrase "substantially water-insoluble" and its variants refer to a substance that does not swell nor dissolve in water or in an aqueous solution at temperatures normally encountered within a body of a mammal. Desirably, the first polymeric layer is substantially free of unreacted isocyanate groups, which may present environmental problems and/or health risks.

Included as an aspect of the present invention is a medical device intended for introduction to the body comprising a substrate suitable for introduction into the body, the surface of the substrate being coated with a cured polymeric composition, the composition comprising a first polymeric layer formed from at least a partial reaction of an aqueous dispersion or emulsion of a polymer having reactive organic acid functional groups present with a polyfunctional crosslinking agent which reacts with the organic acid functional groups, and a second hydrophilic polymeric layer having organic acid functional groups present and being capable of reacting with the crosslinking agent. As described further herein, the first polymeric layer is substantially cross-linked prior to the application of the second polymeric layer. Sufficient functional groups remain from the crosslinking agent to participate in covalent bonding with the second polymeric layer. This covalent bonding, as compared to physical or ionic bonding, allows for excellent adhesion of the lubricous, hydrophilic layer to the first polymeric coating. The coating has excellent wear resistance, lubricity and can be applied in extremely thin layers so as not to affect the mechanical properties of the substrate to which it is applied. Additionally, the adherence of the outer coating is improved over the prior art due to the covalent bonding which occurs between the two coating layers.

In the present context the term "organic acid group" is meant to include any groupings which contain an organic acidic ionizable hydrogen. Examples of functional groupings which contain organic acidic ionizable hydrogen are the carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

The polymer having organic acid functional groups, which is included in the first aqueous coating composition, will be selected duly paying regard to the nature of the substrate to be coated. Typically the polymer in the first coating composition will be selected from homo- and copolymers including vinylic monomer units, polyurethanes, epoxy resins and combinations thereof. The polymer in the first coating composition is desirably selected from polyurethanes, polyacrylates, polymethacrylates, polyisocrotonates, epoxy resins, acrylate-urethane copolymers and combinations thereof having organic acid functional groups. Homo- and copolymers having a substantial amount of organic acid functional groups in their structure, which may act as an internal emulsifier, are also useful. A specific class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly useful.

Examples of water-borne polyurethanes are those supplied under the tradename NeoRez by Zeneca Resins, for instance NeoRez-940, NeoRez-972, NeoRez-976 and NeoRez-981; under the trade name Sancure by B.F. Goodrich, for instance Sancure 2026, Sancure 2710, Sancure 1601 and Sancure 899; and under the tradenames Bayhydrol PR-240, Bayhydrol LS-2033, Bayhydrol LS-2100, Bayhydrol LS-2990 by Bayer AG.

Another specific class of polymers which have shown particularly useful in the first coating composition are acrylate-urethane copolymers, for instance the acrylic urethane copolymer dispersions supplied under the tradenames NeoPac E- 106, NeoPac E- 121, NeoPac E-130 and NeoRez R-973 by Zeneca Resins.

The concentration of the polymer in the first coating composition is desirably from about 2 to about 60 percent by weight and more desirably from about 5 to about 40 percent by weight calculated as solids of polymer compared to the total weight of the first coating composition. The concentration of the hydrophilic polymer in the hydrophilic layer is desirably from about 0.1 to 30 percent by weight, more desirably from about 0.5 to about 5 percent by weight, calculated as solids of hydrophilic polymer compared to the total weight of the second coating composition.

In addition to one or more polymers having organic acid functional groups, the first aqueous coating composition comprises one or more polyfunctional crosslinking agents having functional groups being capable of reacting with organic acid groups. Polyfunctional crosslinking agents having functional groups being capable of reacting with organic acid groups are known in the art. For instance such polyfunctional crosslinking agents have been used for external crosslinking of polyurethanes.

Particularly preferred polyfunctional crosslinking agents for use in the method according to the invention are polyfunctional aziridines and polyfunctional carbodiimides.

Polyfunctional aziridines and polyfunctional carbodiimides and their use as crosslinking agents are known in the art.

The crosslinking agent supplied by Zeneca Resins under the tradename NeoCryl CX 100 and the crosslinking agent supplied by EIT Industries under the tradename XAMA-7 are specific examples of polyfunctional aziridine crosslinking agents which may be used in the method according to the invention, and the crosslinking agent supplied by Union Carbide under the tradename Ucarlink XL-29SE is a specific example of a polyfunctional carbodiimide crosslinking agent which may be used in the method according to the invention.

Among the polyfunctional aziridines useful include the trifunctional aziridine of the following formula:

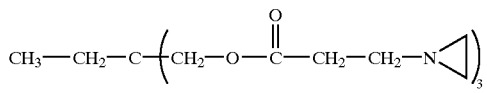

The polyfunctional crosslinking agent is desirably a crosslinking agent having more than two functional groups per molecule. The polyfunctional feature of the crosslinking agent in an important aspect of the present invention to ensure that functional groups of the crosslinking agent covalently bond to both the first polymeric coating and to organic acid groups present in the second (hydrophilic) polymeric coating. Furthermore, it should be noted that a combination of polyfunctional crosslinking agents may be used in the method according to the invention.

The functional groups on the crosslinking agent serves at least two purposes. The first purpose is to crosslink the first polymeric coating. The second purpose is to participate in covalent bonding with the organic acid groups present in the second (hydrophilic) polymeric coating. As such, there should be sufficient functionality in the crosslinking agent to accomplish both purposes. That is, the amount of crosslinking agent used should be sufficient such that enough functional groups are present to substantially crosslink the first polymeric coating with enough unreacted functional groups remaining to covalently bond to the second hydrophilic layer. Furthermore, a substantial number of the molecules of the crosslinking agent should be covalently bonded to both the first polymeric coating and to the second hydrophilic layer.

One indication that insufficient functional groups, either in total or on a molecular basis, from the crosslinking agent are present is the inadequate bonding of the second layer. This is evidenced by the lack of wear resistance and such coatings can be easily wiped off the substrate to which they are applied.

The concentration of the crosslinking agent in the first coating composition is usually in the range from about 0.2 to about 30 percent by weight and preferably in the range from about 0.5 to about 20 percent by weight.

As is known in the art the first aqueous coating composition may include other conventional additives like leveling agents, various stabilizers, pH adjustment agents, defoaming agents, cosolvents, etc. if compatible with the intended use of the coated substrate.

The coating of the first aqueous coating composition is dried so as to obtain a substantially water-insoluble coating layer still including functional groups being reactive with organic acid groups. Hereafter, the obtained dried coating is contacted with a second aqueous coating composition comprising an aqueous solution or dispersion of a hydrophilic polymer having organic acid functional groups, after which the second coating is dried, the hydrophilic polymer thereby becoming bonded to the polymer of the first coating composition through the crosslinking agent.

Hydrophilic polymers for use in hydrophilic lubricous coatings are known in the art. In the method according to the invention any hydrophilic polymer (homo- or copolymer or mixture of one or more of such polymers) may be used provided that it contains organic acid functional groups in its structure which can react with the polyfunctional crosslinking agent having functional groups being capable of reacting with organic acid groups to form a hydrophilic coating becoming lubricous when contacted with an aqueous fluid.

The hydrophilic polymer may comprise monomer units from one or more monomers having organic acid functional groups. Examples of such monomers include acrylic acid, methacrylic acid and isocrotonic acid.

In addition to comprising monomer units from at least one monomer having organic acid functional groups, the hydrophilic polymer may contain monomer units from at least one hydrophilic monomer without any organic acid functional groups, such as vinylpyrrolidone and acrylamide. A useful example of a copolymer for use in or as the hydrophilic polymer in the method according to the present invention is an acrylic acid-acrylamide copolymer. The acrylamide-acrylic acid copolymer supplied by Allied Colloids under the tradename Glascol is a specific example of such a copolymer.

The method according to the invention can be used for the coating of many different kinds of substrates. One field of use of particular interest is the coating of medical articles for use in or on the body, particularly catheters, guide wires, stents, grafts and other body conduits or parts of such articles.

For example, among the useful polymeric substrates include those selected from the group consisting of olefin polymers, particularly polyethylene, polypropylene, polyvinylchloride, polytetrafluoroethylene (PTFE), polyvinylacetate, and polystyrene; polyesters, particularly poly(ethylene terephthalate); polyurethanes; polyureas; silicone rubbers; polyamides, particularly nylons; polycarbonates; polyaldehydes; natural rubbers; polyether-ester copolymers; and styrene-butadiene copolymers. This list is, of course, nonlimiting. Combinations of these materials and composite devices using these materials are contemplated.

In particular, the polymeric substrate can be selected from the group consisting of poly(ethylene terephthalate), polyurethanes, polyethylene, nylon 6, nylon 11 and polyether-ester copolymers.

Examples of useful non-polymeric substrate include those selected from the group consisting of ceramics, metals, glasses and the like.

Also, combinations of polymeric substrates and non-polymeric substrates as well as combinations of one or more polymeric substrates and/or one or more non-polymeric substrates can be coated by the method according to the invention.

The invention will be further illustrated in the following non-limiting examples representing presently preferred embodiments of the invention.

EXAMPLES

Example 1

A first coating composition was prepared by adding the following ingredients successively to a glass beaker under proper agitation until thoroughly mixed.

| | |
|---|---|
| Bayhydrol PR240 | 98 grams |
| Neocryl CX-100 | 2 grams |

Bayhydrol PR240 (from Bayer) is an aliphatic polyurethane dispersion containing sulfonate groups. The waterborne polyurethane supplied has a pH of 6.5–7.5, and the sulfonate groups are in sodium form. Neocryl CX-100 (from Zeneca resins) is a polyfunctional aziridine crosslinking agent.

A second coating composition, as follows, was prepared as follows:

| | |
|---|---|
| Glascol | 1 gram |
| De-ionized water | 98.5 grams |
| 30% sodium chloride | 1.8 gram |
| 34% NH$_4$OH | drops as needed to adjust pH |

Glascol (from Allied Colloids) is an acrylic acid/acrylamide copolymer with molecular weight of approximately 6.5 million and pH of 8.0 (1% aqueous solution). The Glascol and sodium chloride were added into the glass beaker with water, and mixed thoroughly under vigorous agitation. After overnight mixing, a clear solution was obtained. Ammonium hydroxide was added into the beaker with an eyedropper to adjust the pH of the solution to 9.0–10.0.

A third coating composition, as follows, was prepared as follows:

| | |
|---|---|
| The first coating composition | 4 grams |
| The second coating composition | 96 grams |

The first coating composition was added into the beaker containing the second coating composition under agitation, and thoroughly mixed.

A 6 French urethral stent, which is made of ethylene vinyl acetate (EVA), was first coated with the first coating composition, and air dried for 15 minutes. The stent was coated with the third coating composition and air dried for 15 minutes. The stent was finally coated with the second coating composition and air dried for overnight at 50° C. The sample was then packed in a Tyvek pouch and sterilized by ethylene oxide (EtO) gas.

The lubricity of the coated stent upon contact with aqueous medium was determined as a resistance to movement or a coefficient of friction. A portion of the 6 French urethral stent coated with the hydrophilic polymer as described above was placed in a tube filled with saline to hydrate the hydrophilic polymer. The upper part on the stent was connected to a Chattilon Tension tester. A set of rollers was placed directly above the tube in a manner such that hydrated portion goes through the set of rollers. A weight of 400 grams was accurately applied to the roller surface through a sliding mechanism. The Chattilon force gauge and the driving motor were engaged. The hydrated medical device was then pulled through the set of rollers at a pulling speed of 6 inches per minute (15.2 cm/min). As the hydrated portion of the stent coated with the hydrophilic polymer passed the set of rollers, the pulling force of 11.2 grams on the Chattilon gauge was recorded. The coefficient of friction of about 0.028 was determined from the pulling force and the weight applied to the surface. The coefficient of friction (0.028) equals the pulling force (11.2 grams) divided by the weight (400 grams) applied to the surface. The hydration time for the coating was about thirty seconds before commencing the Chattilon Tension tester.

Under similar test conditions a 6 French EVA urethral stent that was not coated with the above-described compositions was tested to have a coefficient of friction of greater than 0.375. With a 400 gram weight applied to the uncoated surface, a 150 gram pulling force was recorded. The 150 gram pulling force, however, was the maximum recordable value on the Chattilon test gauge, so the actual pulling force was somewhat greater than this 150 gram value.

Example 2

A 6 French urethral stent made of EVA containing 10% Triclosan, an antimicrobial compound (from Ciba-Geigy), was coated with the coating compositions and procedures as described in Example 1. The stent was sterilized by EtO.

Example 3

Bacterial adhesion test through dynamic flow model was used to evaluate the coated stents.

The source of infection consisted of a suspension of *Escherichia coli* at a concentration of 1,000 cfu/mL (or colony forming units per milliliter). Bacterial suspensions were created by inoculating a chemostat with a few colonies of the clinical isolate. The chemostat consisted of a continuously stirred reactor which maintained a steady state bacterial count of 1,000,000 cfu/mL. Trypticase soy broth (BBL, Microbiology Systems, Cockeysville, Md.) was the media used to maintain the bacterial concentration in the chemostat.

The chemostat allows for highly adherent, similar genetric expression, and a consistent daily challenge of cells to be used throughout the course of the experiment.

Daily bacterial counts in the chemostat was confirmed by direct microscopy using acridine orange direct counts. (AODC) Subsequent dilutions in the challenge media of natural urine reflect a consistent 1,000 cfu/mL daily challenge.

Natural urine was collected, centrifuged, homogenized, and double filtered sterilized with 0.2 micron filters for the course of the experiment. The urine was divided into thirty 300 mL flasks and refrigerated at 4° C. Prior to use, contamination of the natural urine was checked by overnight growth at 37° C. and subsequently checked by AODC, plate growth on blood sugar, and optical density before being used for the 1,000 cfu/mL challenge.

Growth curves over a 24 hour period to show bacterial growth in the urine was conducted. If the suspensions grew by more than 1 log over a 24 hour period, the urine and inoculant were suspended on ice throughout the course of the experiment. The precaution in this measure was not to let the bacterial suspension grow beyond the intended 1,000 cfu/mL challenge.

A modified infusion pump was used to conduct the study. The infusion pump utilized thirty 10 mL syringes simultaneously inoculating 30 bioreactors. The syringes, containing 10 mL of 1,000 cfu/mL challenge, flowed 10 mL/day of inoculant over the test samples. Every 24 hours, one of the bioreactors was taken off-line and sampled for biofilm growth.

One segment was roll-plated on blood agar and incubated for 24 hours to determine viability of attached cells (Roll Plate Test). One segment was scraped with a sterile scalpel, sonicated for 1 minute, and vortexed for 30 seconds in 100 uL of phosphate buffered solution (PBS). The PBS was then plated on blood agar and incubated for 24 hours to determine growth in cful/mL (Plate Count test). The final segment is stained with Molecular Probes BacLight Live/Dead stain to determine cell viability (Direct Count Test). Cell attachment and viability was determined by direct epi-fluorescent microscopic examination. Measurement parameters were percent area of coverage, and percent of live cells versus dead cells. In accordance with standards traceable to National Institute of Standard Technology (NIST) standards, 20 random fields were examined. Segments deemed to need further microscopic examination were prepared for scanning electron microscopy.

Example 4

The test described in Example 3 was used to compare the bacterial adhesion of the coated stents from Example 1, along with some commercially available hydrogel coated samples.

| Escherichia coli adhesion: | | Day 1 | Day 5 | Day 30 |
|---|---|---|---|---|
| Bardex Lubristent | Plate Count, cfu/mm$^2$ | $9.4 \times 10^2$ | $6.3 \times 10^8$ | $7.1 \times 10^8$ |
| | Percent Coverage | 15 | 80 | 90 |
| Surgitek H$_2$O | Plate Count, cfu/mm$^2$ | $7.0 \times 10^1$ | $5.2 \times 10^8$ | $5.0 \times 10^8$ |
| | Percent Coverage | 5 | 80 | 90 |
| Cook Urological | Plate Count, cfu/mm$^2$ | $2.0 \times 10^1$ | $8.2 \times 10^7$ | $5.4 \times 10^8$ |
| | Percent Coverage | 5 | 80 | 90 |
| Surgitek Lubriflex | Plate Count, cfu/mm$^2$ | $7.3 \times 10^2$ | $3.6 \times 10^7$ | $8.0 \times 10^8$ |
| | Percent Coverage | 10 | 80 | 90 |
| Bardex In-Lay | Plate Count, cfu/mm$^2$ | $3.0 \times 10^3$ | $5.8 \times 10^7$ | $7.4 \times 10^8$ |
| | Percent Coverage | 15 | 80 | 90 |
| Coated samples from Example 1 | Plate Count, cfu/mm$^2$ | 0 | 0 | 0 |
| | Percent Coverage | 0 | 0 | 0 |

The test results indicated that the coated sample from Example 1 had excellent resistant to bacterial adhesion for extended periods of time. It showed no bacterial adhesion during the 30 days period versus other hydrogel coated samples, which showed different level of bacterial adhesion in the first day. All those other coated sample had severe bacterial adhesion after 5 days.

Example 5

Uncoated 6 French EVA stent, the coated stents from Examples 1 and 2 were evaluated in the model described in Example 3. Instead of *Escherichia coli*, two other bacteria were used; i.e. *Pseudomonas aeruginosa* and *Staphylococcus epidermidis*

Pseudomonas aeruginosa

| Pseudomonas aeruginosa Adhesion: | | DAY 1 | DAY 2 | DAY 3 | DAY 4 | DAY 5 |
|---|---|---|---|---|---|---|
| Uncoated 6 French EVA stent | Roll Plate | Positive | Positive | Positive | Positive | Positive |
| | Plate Count (1) | $1.10 \times 10^5$ | $1.60 \times 10^7$ | $4.80 \times 10^7$ | $1.40 \times 10^7$ | $2.30 \times 10^7$ |
| | Direct Count (1) | $5.20 \times 10^5$ | $3.80 \times 10^7$ | $7.90 \times 10^7$ | $4.80 \times 10^7$ | $5.20 \times 10^7$ |
| | % Covered | 80 | 100 | 100 | 100 | 100 |
| | Biofilm Detected | Positive | Positive | Positive | Positive | Positive |
| Coated 6 French EVA stent from Example 1 | Roll Plate | Negative | Negative | Negative | Negative | Negative |
| | Plate Count (1) | 0 | 0 | 0 | 0 | 0 |
| | Direct Count (1) | 0 | 0 | 0 | 0 | 0 |
| | % Covered | 0 | 0 | 0 | 0 | 0 |
| | Biofilm Detected | Negative | Negative | Negative | Negative | Negative |
| Coated 6 French EVA stent from Example 2 | Roll Plate | Negative | Negative | Negative | Negative | Negative |
| | Plate Count (1) | 0 | 0 | 0 | 0 | 0 |
| | Direct Count (1) | 0 | 0 | 0 | 0 | 0 |
| | % Covered | 0 | 0 | 0 | 0 | 0 |
| | Biofilm Detected | Negative | Negative | Negative | Negative | Negative |

Note: (1) units in CFU/mm$^2$

The test results indicated that the coated sample from Examples 1 and 2 had excellent resistant to *Pseudomonas aeruginosa* adhesion for extended periods of time. It showed no bacterial adhesion during the test period as compared to an uncoated sample, which showed different level of bacterial adhesion in the first day.
Staphylococcus epidermidis

| *Staphylococcus epidermidis* Adhesion: | | DAY 1 | DAY 2 | DAY 3 | DAY 4 |
|---|---|---|---|---|---|
| Uncoated 6 | Roll Plate | Positive | Positive | Positive | Positive |
| French | Plate Count (1) | $2.00 \times 10^3$ | $7.80 \times 10^4$ | $5.20 \times 10^5$ | $9.30 \times 10^6$ |
| EVA stent | Direct Count (1) | $7.30 \times 10^3$ | $1.20 \times 10^5$ | $6.00 \times 10^5$ | $6.50 \times 10^7$ |
| | % Covered | 45 | 70 | 85 | 100 |
| | Biofilm Detected | Positive | Positive | Positive | Positive |
| Coated 6 | Roll Plate | Negative | Negative | Negative | Negative |
| French | Plate Count (1) | 0 | 0 | 0 | 0 |
| EVA stent | Direct Count (1) | 0 | 0 | 0 | 0 |
| from | % Covered | 0 | 0 | 0 | 0 |
| Example 1 | Biofilm Detected | Negative | Negative | Negative | Negative |
| Coated 6 | Roll Plate | Negative | Negative | Negative | Negative |
| French | Plate Count (1) | 0 | 0 | 0 | 0 |
| EVA stent | Direct Count (1) | 0 | 0 | 0 | 0 |
| from | % Covered | 0 | 0 | 0 | 0 |
| Example 2 | Biofilm Detected | Negative | Negative | Negative | Negative |

Note: (1) units in $CFU/mm^2$

The test results indicated that the coated sample from Examples 1 and 2 had excellent resistant to *Staphylococcus epidermidis* adhesion for extended periods of time. It showed no bacterial adhesion during the test period as compared to an uncoated sample, which showed different level of bacterial adhesion in the first day.

In the foregoing the invention has been described by means of specific embodiments, but it will be understood that various changes and modifications may be performed without deviating from the scope and spirit of the invention.

What is claimed is:

1. A medical device having a substrate with a hydrophilic coating thereon, said hydrophilic coating comprising:
    a hydrophilic polymer having a sufficient disaffinity to microbes upon contact with an aqueous fluid such that in vivo adherence of said microbes on said coating is limited to substantially prevent biofilm formation thereon by said microbes for up to 5 days in vivo.

2. The device of claim 1, wherein said hydrophilic polymer limits in vivo microbial adherence to less than 10,000 $cfu/mm^2$ on said coating.

3. The device of claim 1, wherein said hydrophilic polymer limits in vivo microbial adherence to less than 1,000 $cfu/mm^2$ on said coating.

4. The device of claim 1, wherein said hydrophilic polymer limits in vivo microbial adherence to less than 100 $cfu/mm^2$ on said coating.

5. The device of claim 1, wherein said hydrophilic polymer limits in vivo microbial adherence to less than 40 percent coverage of a surface of said coating.

6. The device of claim 1, wherein said hydrophilic polymer limits in vivo microbial adherence to less than 20 percent coverage of a surface of said coating.

7. The device of claim 1, wherein said hydrophilic polymer becomes lubricous upon contact with said aqueous fluid to limit in vivo adherence of microbes on said coating.

8. The device of claim 7, wherein said hydrophilic polymer has a coefficient of friction from about 0.02 to about 0.2 upon contact with said aqueous fluid.

9. The device of claim 1, wherein said hydrophilic polymer is selected from the group consisting of copolymers of acrylic acid, methacrylic acid, isocrotonic acid and combinations thereof.

10. The device of claim 1, wherein said hydrophilic polymer is an acrylamide-acrylic acid copolymer.

11. The device of claim 1, wherein said hydrophilic polymer has a molecular weight in the range from about 100,000 to about 15 million.

12. The device of claim 1, wherein said hydrophilic polymer has a molecular weight in the range of from about 150,000 to about 10 million.

13. The device of claim 1, wherein said hydrophilic polymer has a molecular weight in the range of from about 400,000 to about 10 million.

14. The device of claim 1 further including a substantially water-insoluble coating disposed between said hydrophilic coating and said substrate, wherein said water-insoluble coating includes a polymer selected from the group consisting of polyurethanes, polyacrylates, polymethacrylates, polyisocrotonates, epoxy resins, acrylate-urethane copolymers and combinations thereof.

15. The device of claim 14, wherein said hydrophilic polymer is covalently bonded to the polymer of the water-insoluble coating.

16. The device of claim 1, wherein the concentration of the hydrophilic polymer in the hydrophilic coating is from about 0.1 to about 30 percent by weight solids content.

17. The device of claim 1, wherein the concentration of the hydrophilic polymer in the hydrophilic coating is from 0.5 to about 5 percent by weight solids content.

18. The device of claim 1, wherein said device is selected from the group consisting of central venous catheters, dialysis catheters, long term tunneled central venous catheters, peripheral venous catheters, short-term central venous catheters, arterial catheters, pulmonary artery catheters, urinary catheters, long term urinary devices, tissue bonding urinary devices, penile prostheses, vascular grafts, endovascular grafts, vascular catheter ports, wound drain tubes, hydrocephalus shunts, peritoneal catheters, artificial urinary sphincters, urinary dilators, guidewires, ureteral stents, urethral stents, vascular stents, and combinations thereof.

19. The device of claim 1, wherein said device is a catheter.

20. The device of claim 1, wherein said microbes include spherical bacteria, rod-shaped bacteria, spiral bacteria, fungi and combinations thereof.

21. The device of claim 1, wherein adherence of said microbes on said coating is limited to substantially prevent biofilm formation thereon by said microbes for up to 30 days in vivo.

22. The device of claim 1, wherein said hydrophilic polymer limits in vivo microbial adherence to less than 10,000 cfu/mm$^2$ on said coating for up to 30 days in vivo.

23. The device of claim 1, wherein said hydrophilic polymer limits in vivo microbial adherence to less than 10,000 cfu/mm$^2$ on said coating for up to 30 days in vivo.

24. The device of claim 1, wherein said hydrophilic polymer limits in vivo microbial adherence to less than 10,000 cfu/mm$^2$ on said coating for up to 30 days in vivo.

25. The device of claim 1, wherein said hydrophilic polymer limits in vivo microbial adherence to less than 40 percent coverage of a surface of said coating for up to 30 days in vivo.

26. The device of claim 1, wherein said hydrophilic polymer limits in vivo microbial adherence to less than 20 percent coverage of a surface of said coating for up to 30 days in vivo.

27. The device of claim 1 further including a substantially water-insoluble coating disposed between said hydrophilic coating and said substrate.

28. A medical device having a substrate with a coating thereon, said coating comprising:
    a substantially water-insoluble coating on the substrate;
    at least one intermediate layer bonded to the substantially water-insoluble coating; and
    a hydrophilic polymer crosslinked to the at least one intermediate layer, wherein no biofilm is formed on the hydrophilic polymer for up to 5 days in vivo.

29. A medical device having a substrate with a coating thereon, said coating consisting essentially of:
    a hydrophilic polymer wherein no biofilm is formed on the hydrophilic polymer for up to 5 days in vivo.

30. A medical device having a substrate with a coating thereon, said coating consisting essentially of:
    a substantially water-insoluble coating on the substrate;
    at least one intermediate layer bonded to the substantially water-insoluble coating, and
    a hydrophilic polymer crosslinked to the at least one intermediate layer, wherein no biofilm is formed on the hydrophilic polymer for up to 5 days in vivo.

31. A medical device having a substrate with a coating thereon, said coating consisting essentially of:
    a substantially water-insoluble coating on the substrate; and
    a hydrophilic polymer, wherein no biofilm is formed on the hydrophilic polymer for up to 5 days in vivo.

32. A medical device having a substrate with a coating thereon, said coating comprising a hydrophilic polymer selected from the group consisting of copolymers of acrylic acid, methacrylic acid, isocrotonic acid and combinations thereof,
    wherein no biofilm is formed on the coating for up to 30 days in vivo.

* * * * *